Figure 3:
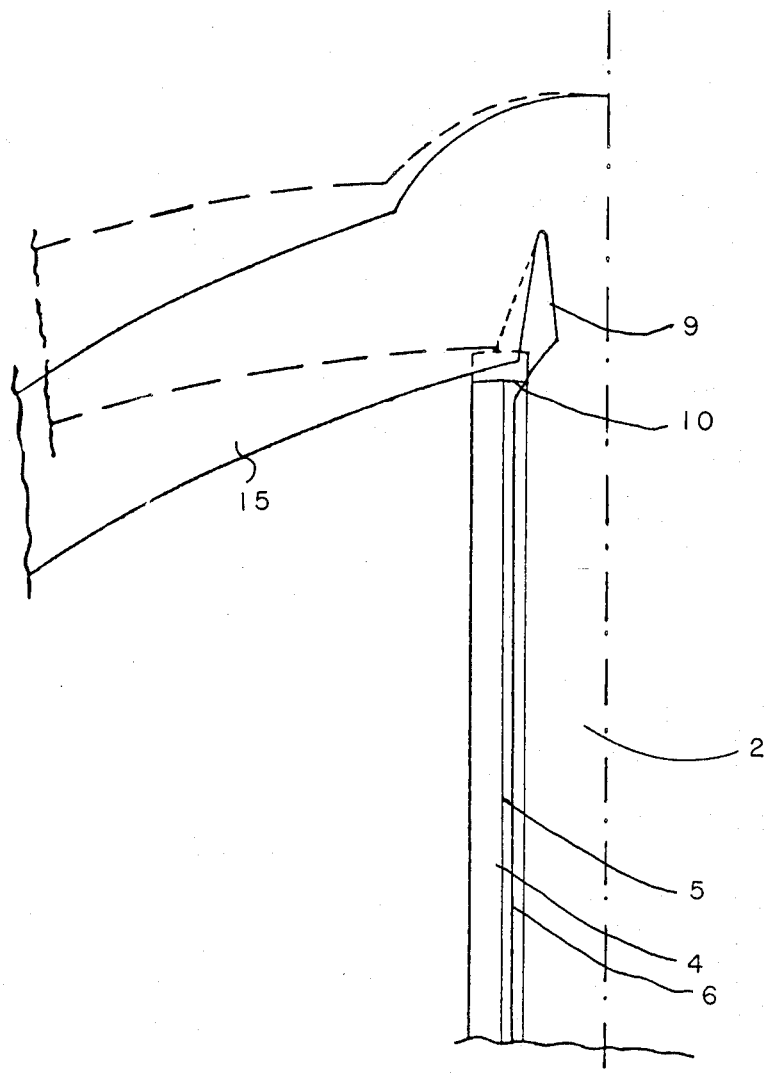

United States Patent [19]

Strubel et al.

[11] Patent Number: 4,724,832
[45] Date of Patent: Feb. 16, 1988

[54] SIZE-VARIABLE INTRAUTERINE PRESSAY AND CONTRACEPTIVE DEVICE

[76] Inventors: Bernd-Jochen Strubel, Strassburger Ring 57, 8700 Würzburg; Karl-Heinz Lurz, Seinsheimstr. 20, 8703 Ochsenfurt, both of Fed. Rep. of Germany

[21] Appl. No.: 871,408
[22] PCT Filed: Sep. 18, 1985
[86] PCT No.: PCT/DE85/00323
 § 371 Date: Apr. 17, 1986
 § 102(e) Date: Apr. 17, 1986
[87] PCT Pub. No.: WO86/01709
 PCT Pub. Date: Mar. 27, 1986

[30] Foreign Application Priority Data

Sep. 18, 1984 [DE] Fed. Rep. of Germany ....... 3434207

[51] Int. Cl.⁴ ................................................ A61F 5/46
[52] U.S. Cl. ..................................... 128/130; 128/127
[58] Field of Search ............... 128/127, 128, 129, 130, 128/131; 604/48, 54, 55

[56] References Cited

U.S. PATENT DOCUMENTS

| 3,405,711 | 10/1968 | Bakunin | 128/130 |
| 3,407,806 | 10/1968 | Hulka et al. | 128/130 |
| 3,410,265 | 11/1968 | Chaft | 128/130 |
| 3,952,734 | 4/1976 | Van Os et al. | 128/130 |
| 4,198,966 | 4/1980 | Kaivola | 128/130 |
| 4,353,363 | 10/1982 | Sopeñaqruesada | 128/130 |
| 4,578,076 | 3/1986 | Luukainen et al. | 128/131 X |

FOREIGN PATENT DOCUMENTS

| 362288 | 10/1922 | Fed. Rep. of Germany . |
| 447562 | 7/1927 | Fed. Rep. of Germany . |
| 2505104 | 2/1975 | Fed. Rep. of Germany . |

Primary Examiner—Robert A. Hafer
Assistant Examiner—Kathleen D'Arrigo
Attorney, Agent, or Firm—Barnes & Thornburg

[57] ABSTRACT

A size-variable intrauterine pessary for adapting to the uterine cavity geometry, which has a rod part with flexible side arms and made from plastic, a coil, more particularly of copper, being optionally wound around the rod part, which has a fastening device for a thread and in which fitting takes place directly in the uterine cavity and which is characterized in that the rod part comprises a body and a control cylinder, that the body is forcibly coupled with the control cylinder, that through the forcible coupling the control cylinder can be moved against the body in the direction of its longitudinal axis and that the rod part has a coupling part into which snaps a fitting device during fitting and said device can be removed again after fitting.

By turning the control cylinder following insertion, the spreading apart of the side arms can be adapted in random manner to the uterine cavity geometry.

13 Claims, 5 Drawing Figures

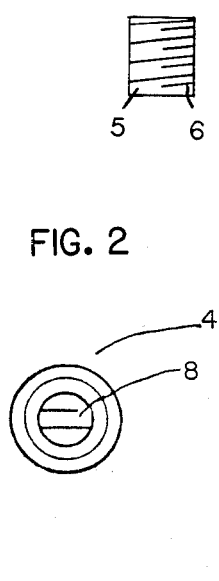
FIG. 1a
FIG. 2
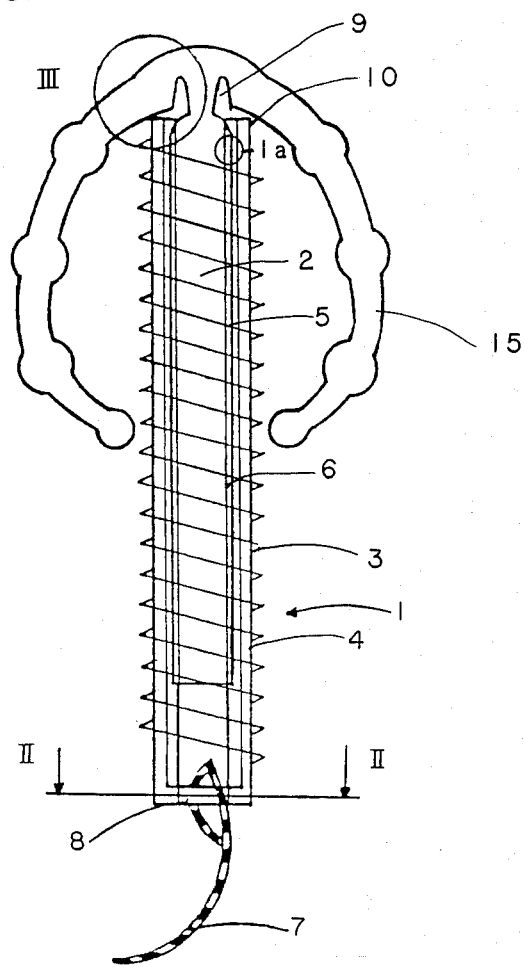
FIG. 1
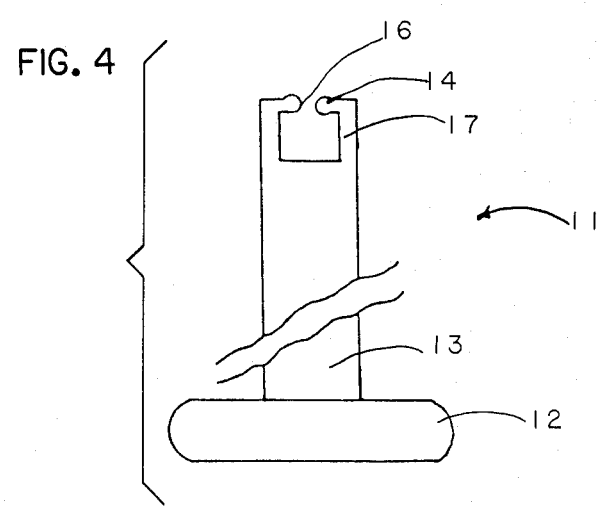
FIG. 4

- - - - SPREAD POSITION
———— INITIAL POSITION

SIZE-VARIABLE INTRAUTERINE PRESSAY AND CONTRACEPTIVE DEVICE

The invention relates to a size-variable intrauterine pessary with an arm adjustable to adapt to the uterine cavity geometry and a central rod-shaped part, which comprises a body and a control cylinder, through whose relative displacement the arms are adjustable and which has a coupling part with which a separate setting device is connected during fitting and which is removed after fitting as well as to a contraceptive device.

The design and size of a intrauterine pessary must be in a correct relationship to the available space in the uterus. Necessarily undesired side-effects result from geometric incompatability. The latter phenomenon has two possibilities, namely a too small intrauterine pessary with the risk of undesired pregnancy through the pessary slipping, whilst the other possibility is of a too large intrauterine pessary, which can generally lead to strong pressure, perforation of the mucosa, bleeding or pain.

A large number of intrauterine pessaries developed over the last few years shows that this problem has been recognized, but also shows that the problem has not as yet been solved. Due to lack of practicability and their complicated nature, adapted intrauterine pessaries have not been adopted into the daily routine.

Admittedly U.S. Pat. Nos. 3,407,806, 3,410,265 and 3,405,711 already disclose intrauterine pessaries adapted to the uterine cavity geometry, but they all suffer from the disadvantage that through a fixed setting and lack of variability of the spring tension when spreading apart the side arms, in the case of a very small uterine cavity, it is not possible to eliminate the risk of pressure, perforation of the mucosa, bleeding and pain. However, in the case of very weak spring tension, the danger exists with a large uterine cavity of the intrauterine pessary slipping and of an undesired pregnancy occurring.

DE-OS No. 2505104 also discloses an intrauterine pessary, which has a rod part with flexible side arms. However, this intrauterine pessary is not intended to adapt to the uterine cavity geometry and instead engages more or less strongly on the cavity walls as a function of the cavity geometry solely due to the specific internal stress of the plastic.

German Pat. No. 447,562 admittedly discloses reciprocally displaceable parts for moving locking levers, but these are rigid locking levers and not flexible side arms. In addition, locking teeth, and not a thread, are provided for adjustment purposes, so that there is only a spreading apart and not a setting or adjustment in the real sense of the term.

German Pat. No. 362,288 discloses an adjustable pessary head, but it has an extremely disadvantageous construction. The pessary head is not adaptable to the uterine cavity geometry and can instead only be adjusted in such a way that it is simply shoved through the narrow cross-section of the uterine cavity inlet.

On the basis of this information, the problem of the present invention is to provide an intrauterine pessary, which can better adapt to the individual geometrical conditions of the uterine cavity due to variable size changes and optimum insertion possibilities.

This problem is solved according to the invention by the features of a size-variable intrauterine pessary with arms which are articulated and constructed in a flexible manner at the upper end of a body and that for spreading apart these arms, the upper edge of a control cylinder is pressed against them.

It is therefore an object of the invention to provide a size-variable intrauterine pessary with plural arms adjusted to adapt to the uterine cavity geometry and a central rod-shaped part, which compries a body and a control cylinder, through whose relative displacement the arms are adjustable and which has a coupling part with which a separate setting device may be connected during fitting and which is removed after fitting wherein the arms are articulated in a flexible manner at the upper end of the body and for spreading apart of the arms, the upper edge of the control cylinder is pressed against.

It is another object of the invention to provide an intrauterine pessary made of plastic.

It is another object of the invention to provide an intrauterine pessary wherein a coil, more particularly made of copper, is wound round a central rod-shaped part.

It is yet another object of the invention to provide an intrauterine pessary wherein a constriction is provided at a connecting point of the body of the intrauterine pessary and the arms thereof.

It is another object of the invention to provide an intrauterine pessary wherein a coupling part is constructed as a web.

It is another object of the invention to provide an intrauterine pessary having a setting device constructed as a turn handle.

It is still another object of the invention to provide an intrauterine pessary wherein a central rod-shaped part or setting device has a fastening means for engaging a thread.

It is a further object of the invention to provide an intrauterine pessary wherein a body and a control cylinder thereof are in screw engagement with one another.

Through the size-variable intrauterine pessary according to the invention, it is now possible, following the insertion of the intrauterine pessary, to spread apart the side arms so as to adapt in an optimum manner to the individual uterine cavity features. This leads to a maximum reduction of side-effects and to a maximum increase in reliability and safety.

Handling can easily be learned through retaining the usual insertion methods and by the extremely simple adjustability of the intrauterine pessary.

The invention also relates to a contraceptive device comprising a size-variable intrauterine pessary and a separate setting device.

The foregoing and other objects, features and advantages of the present invention will become more apparent from the following description when taken in connection with the accompanying drawings which show, for the purposes of illustration only, one embodiment in accordance with the present invention, and wherein:

FIG. 1. shows diagrammatically intrauterine pessary according to the invention.

FIG. 1a the detail Ia of FIG. 1.

FIG. 2. a section along line II—II in FIG. 1.

FIG. 3. the larger scale detail III of FIG. 1.

FIG. 4. diagrammatically and on a large scale a setting device constructed as a turning handle.

Referring now to the drawings wherein like reference numerals are used to designate like parts and more particularly to FIG. 1, there is shown a intrauterine pessary 1 which comprises a body 2, provided with an external thread 6 along its circumference. Two anchorshaped side arms 15 are placed on the upper end of body 2. The connection point of the body 2 to the side arms 15 has a constriction, which is produced by a notch 9, FIG. 3.

On the body 2 is coaxially provided a control cylinder 4 having an internal thread 5 meshing with the external thread 6 of body 2. The meshing of the internal thread 5 of the control cylinder 4 and the external thread 6 of body 2 provides an adjustable screw engagement between the control cylinder 4 and the body 2. The control cylinder 4 is provided on its lower end with a web 8 acting as a coupling part. Thread 7 can also be fixed to web or coupling part 8. A copper coil 3 is fixed to control cylinder 4.

FIG. 4 shows a setting device 11 in the form of a turning handle. The setting device 11 comprises a grip 12 and a shaft 13. At the end of shaft 13 remote from grip 12 are provided two pins 17 which have two inwardly pointing snap heads 14. Between the latter is provided a spacing 16 adapted to the diameter of coupling part 8.

The function of the size-variable intrauterine pessary is briefly described hereinafter.

On inserting the size-variable intrauterine pessary 1, the setting device 11 is connected in cardan or gimbal manner via coupling part 8 to the intrauterine pessary 1. After inserting the intrauterine pessary 1 in the uterine cavity in the usual way, by turning the setting device 11 the upper edge 10, FIG. 3 of control cylinder 4 is pressed against the side arms 15 of the pessary as shown generally at 10. As a result of this pressure, the side arms spread in the direction of the uterus wall until they engage therewith as shown by dashed lines such as 15, FIG. 3.

By moving the intrauterine pessary 1 during fitting, the doctor can establish the time of optimum intrauterine pessary fit. After fixing the pessary 1 in optimum manner in the uterine cavity, the setting device 11 is separated and removed from coupling part 8 by a gentle pulling action.

This size-variable intrauterine pessary makes it possible for the first time to cover in an optimum manner with a single size all the geometrical conditions of the uterine cavity, thereby reducing in an optimum manner the side-effects and greatly increasing reliability and safety.

While we have shown and described only one embodiment in accordance with the present invention, it is understood that the same is not limited thereto but is susceptible to numerous changes and modifications as known to one having ordinary skill in the art, and therefore we do not wish to be limited to the details shown and described herein, but intend to cover all such modifications as are encompassed by the scope of the appended claims.

We claim:

1. A size-variable intrauterine pessary with plural arms adjustable to adapt to a uterine cavity geometry and a central rod-shaped part which comprises a body and a control cylinder, said body and control cylinder being relatively displaceable for adjusting said arms, and which has a coupling part with which a separate setting device may be connected during fitting and which is removed after fitting, wherein the arms are articulated in a flexible manner at the upper end of the body, said control cylinder having an upper edge which is pressed against the arms for spreading the arms apart.

2. A intrauterine pessary according to claim 1, characterized in that the pessary is made from plastic.

3. An intrauterine pessary according to claim 2, further comprising a coil wound around the central rod-shaped part.

4. An intrauterine pessary according to claim 1 further comprising
a constriction disposed at a connecting point of the body to the arms.

5. An intrauterine pessary according to claim 1 wherein the coupling part is constructed as a web.

6. An intrauterine pessary according to claim 1 wherein
the setting device is constructed as a turn handle.

7. An intrauterine pessary according to claim 1 wherein the setting device has a fastening means for engaging a thread.

8. An intrauterine pessary according to claim 1 wherein
the body and control cylinder are in screw engagement with one another.

9. An intrauterine pessary comprising:
plural adjustable arms to adapt to a uterine cavity geometry,
a central body having a constricted member for connecting said body to said arms for spreadable adjustment of the arms and
a control cylinder means adjustably mounted on the central body for engaging at least one of said arms and for adjusting at least one of said arms in relation to said central body in response to an adjustment of the control cylinder with respect to the cylinder body.

10. An intrauterine pessary in accordance with claim 9 wherein the central body and control member are mounted to each other by thread means to produce on rotation of said control member with respect to said body, said spreading of at least one arm.

11. An intrauterine device in accordance with claim 9 further comprising
a coil surrounding said control cylinder.

12. An intrauterine device in accordance with claim 9 wherein said control body has a web means for attachment.

13. An intrauterine assembly comprising
a pessary having plural adjustable arms to adapt to a uterine cavity geometry, a central body having a constricted member for connecting said body to said arms for spreadable adjustment of the arms, a control cylinder means mounted on the central body and adjustable with respect thereto and engaging at least one of said arms for adjustably spreading at least one of said arms in relation to said body,
said control cylinder means having a web means for attachment, and
a setting device comprising a turn handle, a shaft mounted to the turn handle, and at least one snap pin for removably engaging said web means.

* * * * *